Figure 1:
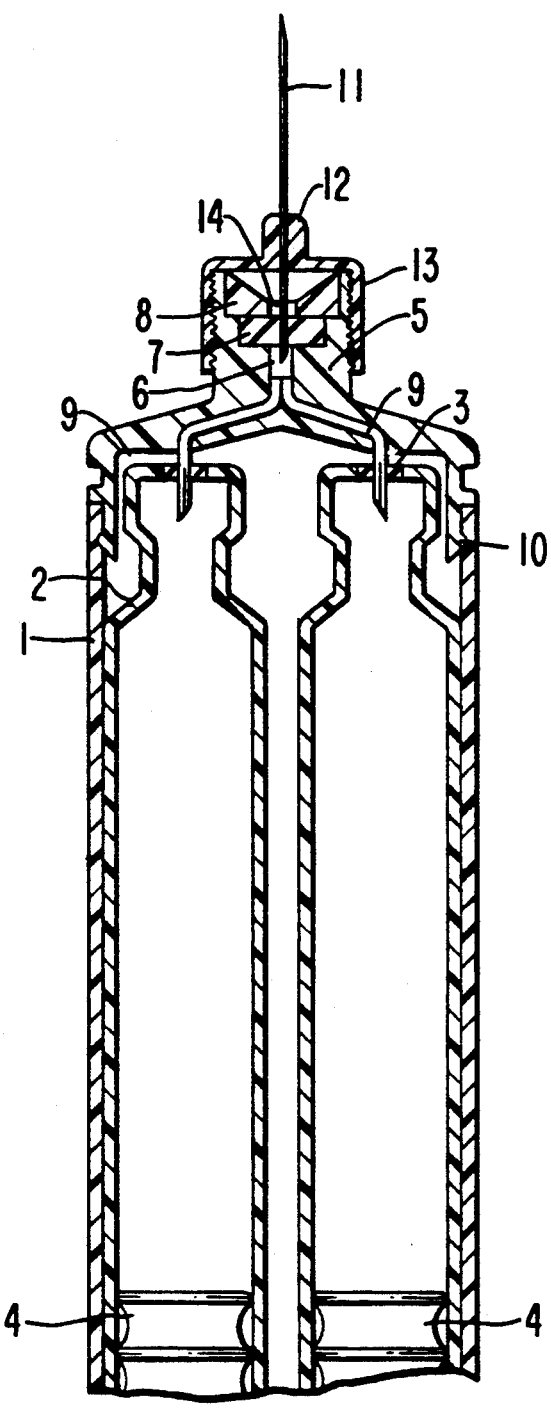

United States Patent [19]
Rex

[11] Patent Number: 5,314,412
[45] Date of Patent: May 24, 1994

[54] MANIFOLD FOR A TWO BARREL SYRINGE

[75] Inventor: Jorn Rex, Roskilde, Denmark

[73] Assignee: Novo Nordisk A S, Bagsvaerd, Denmark

[21] Appl. No.: 701,236

[22] Filed: May 16, 1991

[30] Foreign Application Priority Data

Apr. 17, 1991 [DK] Denmark ................ 689/91

[51] Int. Cl.⁵ .................................. A61M 5/00
[52] U.S. Cl. ................................. 604/191; 604/82; 604/240; 128/762; 222/137
[58] Field of Search ............... 604/82, 85, 86, 187, 604/191, 200, 201, 239–241, 232, 234, 272, 206, 88; 128/762; 222/129, 137, 145

[56] References Cited

U.S. PATENT DOCUMENTS

| | | | |
|---|---|---|---|
| 3,604,410 | 9/1971 | Whitacre | 128/762 |
| 3,730,170 | 5/1973 | Michael | 604/86 X |
| 3,767,085 | 10/1973 | Cannon et al. | 222/137 X |
| 4,381,778 | 5/1983 | Kozam et al. | 604/191 |
| 4,735,616 | 4/1988 | Eibl et al. | 604/191 |
| 4,738,660 | 4/1988 | Lucas | 604/139 |
| 4,843,017 | 6/1989 | Oberhardt et al. | 436/177 |
| 4,874,368 | 10/1989 | Miller et al. | 604/82 |
| 5,097,842 | 3/1992 | Bonn | 128/762 |
| 5,240,146 | 8/1993 | Smedley et al. | 222/137 |

FOREIGN PATENT DOCUMENTS

WO91/0748 1/1991 PCT Int'l Appl. .

Primary Examiner—John D. Yasko
Assistant Examiner—Corrine Maglione
Attorney, Agent, or Firm—Steve T. Zelson

[57] ABSTRACT

The invention relates to an apparatus for simultaneous injection of two different kinds of preparations in a preset proportion.

3 Claims, 2 Drawing Sheets

MANIFOLD FOR A TWO BARREL SYRINGE

This application claims priority of Danish application 689/91 filed Apr. 17, 1991 which is incorporated herein by reference.

The invention relates to an apparatus for simultaneous injection of two different kinds of preparations in a preset proportion.

It is known to use insulin preparations for treating diabetes. Originally such preparations were quick acting and had to be injected in short time intervals. To avoid the inconvenience of such frequent injections, a preparation with a prolonged action was provided. The injection procedure has been eased by the provision of pen-shaped syringes allowing the patients to easily inject themselves with doses which may be easily set by the patient immediately before the injection and may be adapted to the patient's immediate need.

By using insulin preparations having a prolonged action the number of injections a day may be minimized.

However, an injection with a quick-acting preparation is necessary before a meal. To minimize the number of injections, a mixture of the two sorts of preparations is injected before the meal. The mixture contains the amount of quick-acting preparation to cover the need induced by the meal and the amount of preparation with prolonged action to cover the basal need until the time for the next injection. The patient may mix the insulin himself by sucking the wanted doses of the two different types of preparations from two different vials into a syringe. If he wants to use a pen syringe, he has to use in the pen a cartridge with a pre-mixed mixture of the two types in a ratio which has to be chosen once for each filling of the pen.

Since it is necessary to vary the mixture ratio throughout the day, a pen-shaped syringe is desired which may be adapted to two ampoules containing a quick-acting preparation and a preparation with prolonged action, respectively. The pen syringe should further be equipped with means for setting a dose composed of an arbitrarily set dose of one preparation and another arbitrarily set dose of the other preparation, and the composed dose should be injectable by one single injection.

Pen-shaped syringes for injecting set doses from a single ampoule being known, the provision of a two-barrelled pen syringe seems to be only a question of arranging two such syringes parallel with each other and providing a yoke connecting the two injection buttons of the two syringes, so that these buttons may be pressed simultaneously.

However, the needles of the two syringes also should be unified in a single needle, and furthermore the volume of the flow path after the point of union should be as small as possible as this path will by each new injection contain a mixture having the ratio of the preceding injection. A manifold may be molded from a plastic material, which manifold has two pointed needles, each penetrating the rubber closure of the respective cartridges, and ducts leading from the needles to a unifying chamber which may be closed by a rubber membrane. A hypodermic needle which is pointed at both ends may be screwed onto the manifold so that one end pierces the rubber membrane and the other may be used for injecting the usual way.

The plastic material used for the molding must be chosen to allow the use of very thin thread-shaped cores for the ducts, and the plastic materials known as being compatible with the medicine cannot be used for this kind of molding.

Consequently, it is the object of the invention to provide a manifold for a two-barrel pen syringe, which manifold is compatible with the medicine and has a very small dead space in which a mixture having one mixing ratio is transferred from one injection to the succeeding one which may be intended to have another mixing ratio.

The above objects are obtained by a manifold which according to the invention comprises a molded plastic body, a pair of needles each having a sharp end designed for piercing a rubber membrane of a cartridge, the needles being embedded in the plastic and shaped so that their sharp ends project from one side of the body with a spacing bringing them in a position to pierce the rubber membranes of the cartridges in the syringe when the manifold is mounted thereon, and the other end of the needles opening into a mixing chamber from which a third needle leads to the outside of the body projecting from the opposite side thereof and ending in a sharp point. Hereby a manifold is obtained which could be molded with a very high precision allowing the mixing chamber to be minimized.

The mixing chamber may be formed by the meeting ends of the three needles matching together, whereby the chamber is reduced to a mixing point from which the two needle tubes leading from the two cartridges continue in a common third tube forming the injection needle. The needles being embedded in the plastic material of the body are sealingly held in position without any need for welding or soldering the meeting needle ends together.

The mixing chamber may alternatively be provided as a cavity in the plastic body, into which cavity the three needles open.

The plastic body in which the needles are sealingly embedded makes the manifold appear as a disposable unit by which all three needles are changed at the same time.

In another embodiment of the invention the two needles connected to the cartridges open into the cavity at one end thereof, the other end of this cavity being closed by a rubber membrane through which the third needle opens into the cavity.

By this embodiment the body may be provided with a thread for receiving a hub with a double pointed needle so that one end of this needle pierces the membrane which closes the cavity. This way a manifold is provided by which the injection needle may be changed without changing the needles connected to the cartridges. The thread may likewise be so accurately provided that one end of the needle just penetrates the membrane, allowing the depth of the mixing chamber to be minimized.

As the diameter of the chamber is kept very small, it is appropriate to design the holder for the membrane covering the cavity as a needle guide having a diameter corresponding to the diameter of the chamber.

Figure 2:
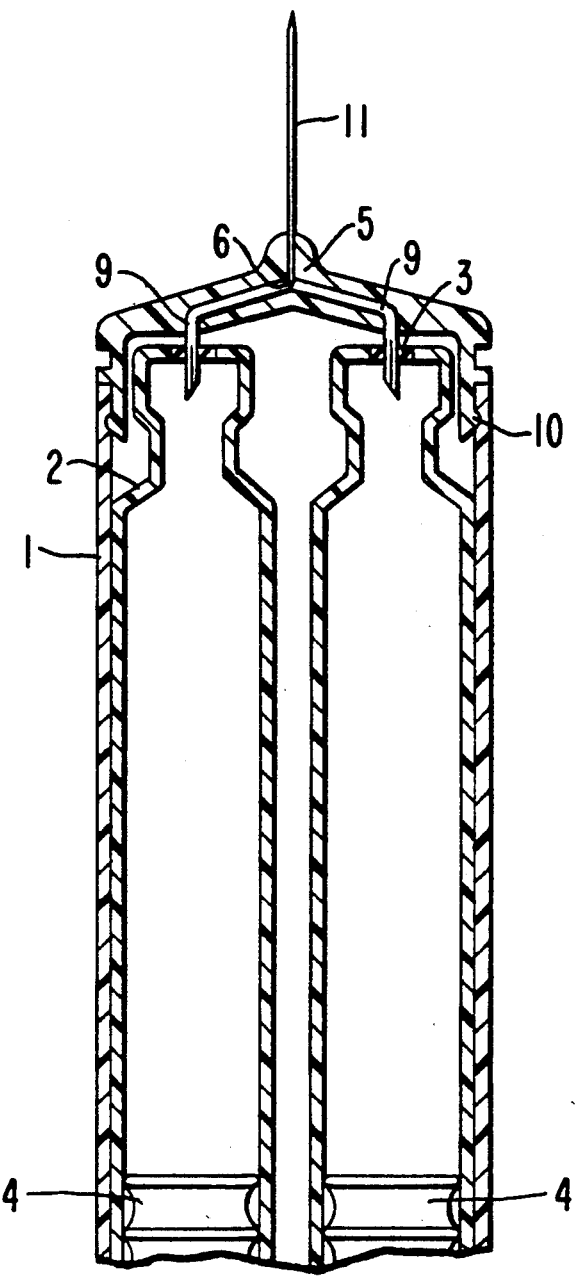

Below, the invention is described in further detail by reference to the drawing, in which FIG. 1 shows schematically a sectional view of an end part of a two-barrel pen syringe with a manifold having a mixing chamber appearing as a cavity in the body, and FIG. 2 shows a view as in FIG. 1 with a manifold having the mixing chamber minimized to a mixing point.

In FIG. 1 the housing of a pen syringe has a wall 1 surrounding two medicine cartridges 2 each being at its front end closed by a rubber membrane 3. At their rear ends the cartridges are closed by pistons 4 which are influenced by the dosing mechanism to press out optional doses from each cartridge.

A manifold comprises a molded plastic body 5 having at its front end a mixing chamber 6 being forwardly closed by rubber membrane 7 secured by a needle guide 8 pressed, bonded or welded into the body. Two needles 9 are embedded in the plastic body leading from the mixing chamber 6 to the outside of the body from the rear side of which they project having at their projecting ends sharp points spaced by a distance corresponding to the distance between the centers of the rubber membranes 3 of the cartridges 2 in the syringe housing. At its rear end the manifold is provided with a snap lock 10 by which the manifold is secured to the housing with the sharp ends of the needles 9 passing through the rubber membranes 3 of the cartridges 2.

The needles 9 are shown leading to the bottom of the mixing chamber, the base area of which may be made even smaller than the total area of the two neighboring ends of the needles 9 as only the openings of the needles have to be free. The needles could also lead through the side walls of the mixing chamber, the base area of which is then only limited by the fact that an injection needle 11 should be allowed to be received in the chamber.

The injection needle 11 is of the well known type being pointed at both ends and being mounted in a hub 12 having an internally threaded ring 13 which may be screwed onto an external thread on the part of the body 5 surrounding the mixing chamber 6, the membrane 7, and the needle guide 8.

The needle guide 8 which secures the membrane 7 in the body 5 has a central bore 14 which is the same size as the base of the mixing chamber 6 and placed opposite this chamber to ensure that the injection needle when passed through the needle guide 8 will pass into the interior of the chamber 6.

In FIG. 2 the same reference numbers are used for the same parts as in FIG. 1. The meeting ends of the needles 9 connected to the cartridges 2 are cut to form a V in which a correspondingly cut end of the injection needle 11 is received all three needles being embedded in the plastic body whereby leaks between meeting end faces are sealed by the plastic which is compatible with the medicine.

I claim:

1. Manifold for a two-barrel pen syringe for administering two different kinds of medicine, said syringe having two parallel cartridges each containing a different kind of medicine and each sealed at their outlet end with a rubber membrane, said manifold comprising:
    a molded plastic body;
    a mixing chamber being formed as a cavity within said plastic body;
    a first, second and third needle each having two ends, a first sharp end and a second end opening into said mixing chamber;
    said mixing chamber being open at one end thereof for one end of said first and second needles, the other end of the mixing chamber being closed by a membrane through which one end of said third needle must pass to open into said cavity;
    said first and second needles being embedded in said molded plastic body and having said first sharp ends project from one side of said molded plastic body with a spacing bringing them in a position to pierce rubber membranes of cartridges in a syringe when the manifold is mounted thereon; and
    said third needle having its first sharp end project outside of said molded plastic body from a side opposite the sharp ends of said first and second needles.

2. Manifold according to claim 1 wherein said body further comprises a thread for receiving a hub and said third needle one end of which pierces the membrane closing the cavity.

3. Manifold according to claim 2, wherein the membrane is fixed over the cavity by a needle guide having an opening corresponding to the opening of the mixing chamber.

* * * * *